United States Patent [19]

Decor

[11] 3,996,292
[45] Dec. 7, 1976

[54] PROCESS FOR THE PREPARATION OF ALIPHATIC DIALDEHYDES

[75] Inventor: Jean-Pierre Decor, Villeurbanne, France

[73] Assignee: Rhone-Poulenc S.A., Paris, France

[22] Filed: Oct. 7, 1974

[21] Appl. No.: 512,983

[30] Foreign Application Priority Data

Oct. 10, 1973 France .............................. 73.36158

[52] U.S. Cl. ........................................... 260/601 R
[51] Int. Cl.$^2$ ........................................ C07O 47/12
[58] Field of Search ................................ 260/601 R

[56] References Cited

UNITED STATES PATENTS 3,517,066  6/1970  Gurien et al. .................. 260/601 R

OTHER PUBLICATIONS

Fleischmann et al., Chem. Abstracts, vol. 74, 49006y, 1971.

*Primary Examiner*—James O. Thomas, Jr.
*Assistant Examiner*—W. B. Lone
*Attorney, Agent, or Firm*—Cushman, Darby & Cushman

[57] ABSTRACT

Aliphatic dialdehydes are prepared in good yield from the corresponding acid chlorides by reduction with hydrogen and a palladium catalyst in the presence of a tertiary amide.

7 Claims, No Drawings

PROCESS FOR THE PREPARATION OF ALIPHATIC DIALDEHYDES

The present invention relates to a process for the preparation of aldehydes by reduction of organic acid chlorides by hydrogen and a palladium catalyst.

The reduction of acid chlorides to the corresponding aldehydes by means of hydrogen and palladium is a process well known to those skilled in the art, the ROSENMUND reaction. The essential characteristic of this process is the use of a palladium catalyst the activity of which has in general been lowered by poisoning with quinoline or a sulphur-containing compound. The presence of these inhibitors or regulators makes it possible to make the reaction selective, thus very greatly limiting the subsequent reduction of the aldehyde to the corresponding alcohol and hydrocarbon; however, these inhibitors reduce the catalytic activity and the resistance to aging. It has also been proposed, for the purpose of increasing the yield of aldehyde, to use, simultaneously with the customary catalyst regulators (quinoline or sulphur-containing compounds), alkaline salts of organic acids which fix the hydrochloric acid or hydrogen chloride liberated (see, for example, U.S. Pat. No. 3,517,066).

An improved process has now been found, according to the present invention, for the preparation of aliphatic dialdehydes by reduction of aliphatic dicarboxylic acid dichlorides by hydrogen and a palladium catalyst. This process is characterized in that the reaction is carried out in the presence of a tertiary amide. The reduction process can now be carried out at a moderate temperature with increased selectivity, using a reduced amount of catalyst. Furthermore, the fact that quinoline or sulphur-containing compounds are not introduced makes it possible to have a more active catalyst of greater working life.

Suitable tertiary amides for the present process can be either linear (straight) or branched, or cyclic. Amongst these tertiary amides there may be mentioned the amides of the formula:

$$R-CO-N\begin{matrix}R^1\\R^2\end{matrix} \qquad (I)$$

in which $R^1$ and $R^2$, which may be identical or different, each represents a straight or branched, saturated aliphatic group having at most 6 carbon atoms, a cycloaliphatic group having 5 or 6 nuclear carbon atoms, or a phenyl, phenylalkyl or akylphenyl group, of which the alkyl substituent of the phenyl group contains at most 4 carbon atoms, or $R^1$ and $R^2$ together form a saturated or unsaturated divalent radical having 4 to 5 carbon atoms, and R is as defined under $R^1$ and $R^2$ or represents a hydrogen atom or R forms together with one of $R^1$ and $R^2$, a divalent radical having from 3 to 5 carbon atoms.

Amongst the amides which correspond to the general formula (I), the following are preferred:

"Linear" amides in which $R^1$ and $R^2$ represent straight or branched alkyl groups having at most 4 carbon atoms, and R has the same meaning or represents a hydrogen atom; and Cyclic amides in which one of $R^1$ and $R^2$ represents a straight or branched alkyl group having at most 4 carbon atoms, whilst the other forms, with the radical R, a divalent radical having from 3 to 5 carbon atoms, Amongst the amides which can be used, the following may be mentioned by way of illustration: N,N-dimethylformamide, N,N-dimethylpropionamide, N,N-dimethylisobutyramide, N,N-dimethylacetamide, N,N-diethylacetamide, N,N-dibutylacetamide, N-methylpyrrolidone, N-ethylpyrrolidone, N-methylpiperidone, N-methylcaprolactam, N-methylformanilide, N-methylacetanilide, N-acetylpyrrolidine and N-acetylpyridine. Amongst these, dimethylformamide, dimethylacetamide and N-methylpyrrolidone, which are commonly used in industry, are advantageously employed.

The amount of tertiary amide which is used varies depending on the nature of the aliphatic dicarboxylic acid chloride. Where the two chloroformyl groups of the dicarboxylic acid chlorides are separated by at least 6 carbon atoms, the risk of forming cyclised by-products is slight and good selectivity can be achieved even if only small amounts, for example from $10^{-5}$ and $10^{-1}$ mol of tertiary amide per chloroformyl group, of tertiary amides are used. Where the two chloroformyl groups in the dicarboxylic acid chlorides are separated by fewer than 6 carbon atoms (as in, for example, succinic and glutaric acid dichlorides), the risk of forming cyclised by-products is high and it is necessary to employ larger quantities of tertiary amide. These quantities can easily be determined by those skilled in the art, if necessary by means of preliminary tests; the optimum amounts of tertiary amides can thus be as much as, or exceed, one mol per chloroformyl group employed. In the case of the reduction of the succinic and glutaric acid chlorides, the ratio $$\frac{\text{mol of amide}}{\text{chloroformyl group}}$$

is advantageously from 1 to 3.

It is thus possible, in appropriate cases, to use the tertiary amide as the reaction solvent. If desired, the reduction reaction can be carried out in the presence of a solvent which is inert under the reaction conditions, such as hydrocarbons, such as xylene, toluene, benzene, tetralin and decalin, or ethers such as dioxane.

The aliphatic dicarboxylic chlorides have the formula:

$$ClCO - X - COCl$$

in which X represents a straight or branched alkylene group. The reduction process according to this invention is in particular applicable to the dicarboxylic acid chlorides in which X represents a straight chain alkylene group containing from 2 to 10 carbon atoms, this alkylene group optionally being substituted by one or more straight or branched alkyl groups having at most 4 carbon atoms. Preferably, X represents a straight chain alkylene group having from 2 to 10 carbon atoms, this alkylene group being optionally substituted by 1 to 2 straight or branched alkyl groups having at most 4 carbon atoms.

The chlorides of the following dicarboxylic acids are typical: succinic acid, methylsuccinic acid, dimethylsuccinic acid, ethylsuccinic acid, glutaric acid, methylglutaric acids, dimethylglutaric acids, dipropylglutaric acids, diethylglutaric acids, adipic acid, methyladipic acids, dimethyladipic acids, 4-methyl-2-propyl-hexanedioic acid, pimelic acid, 2- (or 3-) methyl-heptanedioic acid, 3-ethylheptanedioic acid, 2,6-dipropylheptanedioic acid, 5-methyl-2-propyl-heptanedioic acid, suberic acid, 2,7-dimethyl-octanedioic acid, azelaic acid, 3-methyl-nonanedioic acid, sebacic acid, 2,5,9-trimethyl-decane-1,10-dioic acid, undecane-1,11-dioic acid and dodecane-1,12-dioic acid. These acids are described, for example, in the Treatise on Organic Chemistry by V. GRIGNARD — volume X, 1939 edition.

The amount of palladium catalyst employed is not critical. It is usually from 0.05 to 1 g., preferably from 0.1 to 0.5 g. of palladium per chloroformyl group. The catalyst is usually deposited on a support. The palladium content is in general from 0.5 to 25% by weight. The nature of the support is not critical and can be, for example, an active charcoal, alumina or silica. It is also possible to use catalysts based on palladium deposited on barium sulphate or calcium sulphate.

The process according to the present invention is suitably carried out in a stream of hydrogen at atmospheric or sub-atmospheric pressure. The reaction can also be carried out in a closed vessel under a super-atmospheric pressure of hydrogen. The temperature is in general from 20° to 150° C., preferably from 50° to 80° C.

The process can be put into practice in various ways. For example, the acid dichloride can be introduced gradually or all at once into the reaction medium containing the tertiary amide, the catalyst and, if desired, a solvent. It is also possible to mix the acid dichloride and the tertiary amide beforehand and introduce this mixture into the reactor containing the catalyst and, optionally, solvent. The dialdehydes can be isolated from the reaction medium by any known means.

Aliphatic dialdehydes can be used for the leather's tanning (German application Pat. No. 2,261,657. Kirk-Othmer: Encyclopedia of Organic Chemistry, vol. 12– p 330), and also as reticulating agents for the preparation of ion-exchange resins (French Pat. No. 2,063,975) it is also possible to prepare aminoacids from dialdehydes such as the diaminopinelic acid from glutaric aldehyde [Industrial Engeneering Chemistry 2 308 (1963)); French Pat. No. 1,255,546].

The following Examples further illustrate the present invention.

EXAMPLE 1

84.5 g. of glutaroyl chloride and 87.12 g. of dimethylacetamide are mixed at 0° C., in an Erlenmeyer flask, 210 ml. of toluene are added and this solution is then run, over the course of 1 hour, into a flask which is maintained at 30° C., and contains 17.2 g. of dimethylacetamide, 10 g. of catalyst (palladium deposited on carbon black containing 10% by weight of metal) and 790 ml. of toluene.

Whilst the solution is being run in, the reactor is kept under a stream of hydrogen at the rate of 600 l/hour. When all the solution has been run in, the mixture is cooled to 0° C., the contents of the reactor are filtered and the glutarodialdehyde in the filtrate is determined by vapour phase chromatography. It is found that the degree of conversion of the glutaroyl chloride is 100% and that the yield of glutaraldehyde determined is 88% (confirmed by the oximation method).

A controlled amount of a stream of dry hydrogen chloride is introduced so as to neutralise the residual dimethylacetamide, and the toluene solution is then washed. 31 g. of glutaraldehyde, boiling point: Eb8:71° C., are isolated by distillation.

If the same process is carried out without adding tertiary amide (dimethylacetamide), the yield of glutaraldehyde determined is not more than 40%.

EXAMPLE 2

0.5 g. of catalyst (palladium on charcoal, containing 10% by weight of metal) and 30 ml. of distilled toluene are introduced into the reactor and the dropping funnel is charged with 4.225 g. of glutaroyl chloride, 14.87 g. of N-methylpyrrolidone and 10 ml. of toluene. The mixture is run in all at once, at 30° C. The flask is kept at 30° C., for 3 hours under a stream of dry hydrogen at the rate of 30 l/hour. After filtering off the catalyst, the yield of dialdehyde is found to be 69% by chromatography and by determining the aldehyde groups by oximation.

EXAMPLE 3

0.1875 g. of catalyst (identical to that used in the preceding Example), 35 ml. of toluene and 10.41 microliters of dimethylacetamide are placed in the reactor and a mixture consisting of 4.575 g. of adipoyl chloride and 15 ml. of toluene is run in all at once. The mixture is heated to 70° C., for 2 hours under a stream of hydrogen at the rate of 20 l/hour.

After filtration, chromatography and oximation determination show that no adipoyl chloride remains. The yield of dialdehyde is 55%.

EXAMPLE 4

0.125 g. of palladium on charcoal (identical to that used in the preceding Examples), 35 ml. of toluene and 3.47 microliters of dimethylacetamide are placed in the reactor. 5.275 g. of suberoyl chloride and 15 ml. of toluene are introduced into the dropping funnel; this solution is run all at once into the reactor. The reactants are then kept for 2 hours 20 minutes at 70° C., under a stream of hydrogen at the rate of 30 l/hour.

The yield of dialdehyde is shown to be 85%, by chromatography. Distillation gives a fraction of boiling point 0.3 : 72.5° C., weighing 1.71 g. and corresponding to the pure dialdehyde (melting point of the corresponding dioxime : 152° C.).

EXAMPLE 5

0.125 g. of palladium on charcoal (as in the preceding Examples), 35 ml. of distilled toluene and 3.47 microliters of dimethylacetamide are placed in the reactor. 6.675 g. of dodecanedioyl chloride and 15 ml. of toluene are introduced into the dropping funnel and this solution is then run all at once into the reactor. The reactants are now kept for 2 hours 50 minutes at 70° C., under a stream of hydrogen at the rate of 30 l/hour.

The yield of dialdehyde is shown to be 84.5%, by chromatography. Distillation gives the dialdehyde (boiling point $_{0.4}$ : 114° – 115° C.) in a yield of 84% (melting point of the corresponding dioxime: 150° C.).

I claim:

1. Process for the preparation of an aliphatic dialdehyde which comprises reducing with hydrogen at a temperature of 20° –150° C. a dicarboxylic acid chloride wherein the two chloroformyl groups of the dicarboxylic acid chloride are separated by at least 6 carbon atoms and having 6–18 carbon atoms in the alkylene group joining the two chloroformyl groups, in the presence of a catalyst consisting essentially of palladium, optionally deposited on a support, and in the presence of $10^{-5}$ to $10^{-1}$ mols, per chloroformyl group, of a tertiary amide having the formula

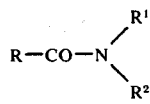

in which:

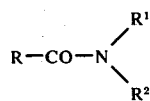

R¹ and R² independently represent a straight or branched aliphatic group having at most 6 carbon atoms, a cycloaliphatic group having 5 or 6 ring carbon atoms, or a phenyl, phenylalkyl or alkylphenyl group, the alkyl substituent of which phenyl group contains at most 4 carbon atoms, or R¹ and R² together form a saturated or unsaturated divalent radical having 4 or 5 carbon atoms, and R is as defined for R¹ and R² or represents hydrogen or forms together with one of the radicals R¹ and R², a divalent radical having from 3 to 5 carbon atoms.

2. Process according to claim 1 in which R¹ and R² each independently represents a straight or branched alkyl group of at most 4 carbon atoms and R is as defined under R¹ and R² or represents a hydrogen atom.

3. Process according to claim 1 in which the tertiary amide is N,N-dimethylacetamide.

4. Process according to claim 1 in which the tertiary amide is N-methylpyrrolidone.

5. Process according to claim 1, in which the acid chloride has the formula:

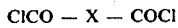

in which X represents a straight chain alkylene group having from 6 to 10 carbon atoms, optionally substituted by 1 or 2 straight or branched alkyl groups having at most 4 carbon atoms.

6. Process according to claim 5 in which the acid chloride is suberoyl chloride or dodecanoyl chloride.

7. Process according to claim 1 which comprises reducing suberoyl chloride or dodecanoyl chloride in the presence of N,N-dimethylacetamide, dimethylformamide or N-methylpyrrolidone at a temperature from 50° to 80° C.

* * * * *